United States Patent [19]

Gencarelli et al.

[11] Patent Number: 4,528,381

[45] Date of Patent: Jul. 9, 1985

[54] PROCESS FOR MAKING TRIAZOLES

[75] Inventors: Richard A. Gencarelli, Waterbury; Edward L. Wheeler, Watertown, both of Conn.

[73] Assignee: Uniroyal, Inc., Middlebury, Conn.

[21] Appl. No.: 411,945

[22] Filed: Aug. 26, 1982

Related U.S. Application Data

[63] Continuation-in-part of Ser. No. 304,524, Sep. 21, 1981.

[51] Int. Cl.$^3$ .............................................. C07D 249/18
[52] U.S. Cl. .................................... 548/257; 548/259
[58] Field of Search ................................ 548/257, 259

[56] References Cited

U.S. PATENT DOCUMENTS

| | | | |
|---|---|---|---|
| 3,227,726 | 1/1966 | Levy | 548/257 |
| 4,363,914 | 12/1982 | Long et al. | 548/257 |
| 4,367,337 | 1/1983 | Sullivan | 548/257 |
| 4,424,360 | 1/1984 | Hagedorn | 548/260 |

FOREIGN PATENT DOCUMENTS

| | | | |
|---|---|---|---|
| 2822506 | 12/1978 | Fed. Rep. of Germany | 548/257 |
| 5151576 | 11/1980 | Japan | 548/257 |
| 1581407 | 12/1980 | United Kingdom | 548/257 |

Primary Examiner—Donald G. Daus
Assistant Examiner—G. Hendricks
Attorney, Agent, or Firm—John A. Shedden

[57] ABSTRACT

The invention provides a process for preparing triazoles comprising reacting a compound having the structural formula

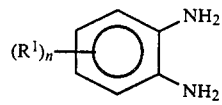

with a compound having the formula

R—ON=O in the presence of $C_6$–$C_{10}$ alkanol, wherein n is 0, 1 or 2, R is $C_6$–$C_{10}$ alkyl and $R^1$ is hydrogen or $C_1$–$C_{10}$ alkyl.

3 Claims, No Drawings

PROCESS FOR MAKING TRIAZOLES

This is a continuation-in-part of U.S. patent application Ser. No. 304,524, filed Sept. 21, 1981.

FIELD OF THE INVENTION

The present invention relates to methods of preparation and purification of triazoles and in particular involves a process in which distillation is not needed to obtain a product of higher purity.

BACKGROUND OF THE INVENTION

Triazoles, especially tolyltriazole, are corrosion inhibitors used for antifreeze and are also used in water treatment applications. Tolyltriazole is manufactured by reacting o-toluenediamine with sodium nitrite and hydrochloric acid. The crude material is then distilled under reduced pressue to give a white solid. This material is sold as such or as an aqueous solution. The disadvantage to this process is that the product must be distilled, a procedure which may be hazardous (C&E News, May 14th, 1956, reports that an explosion occurred during benzotriazole distillation).

U.S. Pat. No. 3,637,514 discloses a method of preparation of tolyltriazole in which a fractional distillation procedure is used. Similarly, in Heterocyclic Compounds, Elderfield, (1961), volume 7, chapter 5, pages 384-425, no suggestion is made of a procedure to prepare tolyltriazole without the use of distillation. Organic Syntheses, collective volume 3, pages 106-108 teaches a method of preparation of 1,2,3-benzotriazole in which the product is distilled.

SUMMARY OF THE INVENTION

In the instant invention a process is utilized in which triazoles are prepared by reacting vicinal aromatic diamino compounds with $C_6$-$C_{10}$ alkyl nitrites using $C_6$-$C_{10}$ alkanols as organic solvents from which the product is extracted as a salt. A product having a degree of purity improved over such triazoles made by previously known methods is obtained when extracting the product/alcohol mixture with caustic. Most of the impurities and unreacted reagents remain in the alcohol layer. The aromatic triazole is isolated by neutralization with acid. If desired, the triazole salt solution may be further purified by heating in the presence of charcoal, such as Norite A (trademark) followed by filtration and precipitation of the free triazole with an acid.

An advantage of the invention is that $C_6$-$C_{10}$ alkyl nitrites are used instead of sodium nitrite and acid. It is a further advantage that the reaction mixture is lighter in color and distillation for purification is not required. A still further advantage of the invention is that essentially pure triazole can be reprecipitated from water.

The aromatic triazoles are prepared according to the general equation:

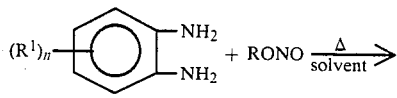
$+ RONO \xrightarrow{\Delta}{solvent}$

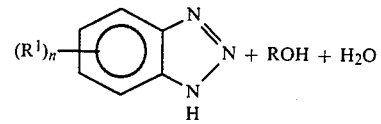
$+ ROH + H_2O$ wherein n is zero, 1 or 2; R is $C_6$-$C_{10}$ alkyl; and $R^1$ is hydrogen or $C_1$-$C_{10}$ alkyl.

The starting vicinal diamino compound may be, for example, 1,2-diaminotoluene, o-penylenediamine, 3- or 4-t-butyl-1,2-diaminobenzene, or 3- or 4-ethyl-1,2-diaminobenzene.

The starting alkyl nitrite compound has the structure R—ON=O wherein R is $C_6$-$C_{10}$ alkyl, hexylnitrite, 2-ethylhexylnitrite, octylnitrite, or decylnitrite.

To the diamino compound in organic solvent is added the alkylnitrite compound over the period of 0.5-3 hours, preferably about 1-1.5 hours which usually results in an exothermic reaction wherein the temperature may rise to as high as 150° C.

The reaction of the diamine with the nitrite compound may be carried out at a temperature of 15°-150° C., preferably 90°-120° C. over a period of 1-15 hours, usually 1-6 hours including nitrite addition period of 0.5-3 hours, preferably 1-1.5 hours.

It was found that this reaction has an induction period when below 90° C. This induction period is reduced by adding 3-5 mole percent of aromatic triazole (based on the diamine) to the reaction mixture before the addition of alkyl nitrite is started, and it is eliminated by running the reaction above 90° C. In fact the reaction can be run at 90°-120° C. without adding aromatic triazole and no induction period is observed.

The molar ratio of aromatic diamine to alkyl nitrite is approximately 1/0.9-1/1.2, preferably 1/1. The amount of a solvent with respect to the reactants is approximately 1/1-5/1 by weight.

It is advantageous to prevent the reaction mixture from being exposed to light.

The product of the above reactions is extracted as a water soluble salt by treating the above mixtures of the triazole and alcohol with aqueous caustic. The caustic may be any alkali or alkali earth metal hydroxide preferably sodium hydroxide or potassium hydroxide. The caustic is diluted with water to a 1-50% by weight concentration, preferably 5%. About 1-1.2 moles preferably 1.05 moles of caustic is added per mole of diamine starting material, sufficient to form a salt.

In practice about 800 ml of water and caustic per mole of product are added to the reaction mixture for the purpose of separating the aqueous from the alcohol layer.

After removal of the water layer, it is advantageous to wash the alcohol layer with an additional 200 ml of water per mole of product, then combine the two water layers containing the product. Neutralization of the aqueous caustic solution causes crystallization of the product, which is removed from the water by appropriate means such as filtration.

It has been found that when mixed o-toluenediamines are used as the starting amines to generate a solution of alkali metal tolyltriazoles it is preferred to have said salt solution at an approximately 10-15 percent by weight concentration. Higher concentrations of the triazole salt do not purify as well because lower water levels tend to trap some of the alcohol and consequently some of the impurities and residual reactants. A ca. 13 percent solution gives a good separation of the organic solvent from the triazole salt solution.

The reaction of the diamine with the nitrite compound is carried out in a $C_6$–$C_{10}$ alcohol. Although any $C_6$–$C_{10}$ alkanol may be used, primary alcohols such as n-hexanol, n-heptanol, n-octanol, 2-ethylhexanol, 2-decanol are preferred. The most preferred alcohol is 2-ethylhexanol.

EXAMPLE 1

Preparation of Tolyltriazole

In a 2 liter, four-necked, round-bottom flask equipped with a thermometer, stirrer, dropping funnel, and a gas inlet tube (for nitrogen) with condenser were placed 122 g o-toluenediamine (TDA) and 200 g 2-ethyl-hexanol. The flask was wrapped with tin foil, heated to 90°–95° C. and 172.8 g 92.0% 2-ethylhexyl nitrite was added over 40 minutes, during which time the temperature rose to as high as 118° C. The mixture was heated to 90°–95° C. for one hour after all the nitrite had been added, and then 190 ml of 6N NaOH diluted with water to 800 ml were added. The mixture was transferred to a separatory funnel and the water layer removed. The alcohol layer was washed with 200 ml of water. The combined water layers were washed with 100 ml of 2-ethylhexanol, heated with 10 gm of charcoal (Norite $A_{TM}$) to 90° C. for 10 minutes to eliminate traces of discoloration, filtered, cooled and neutralized to pH 8.2 with 6N HCl. After the product had crystallized, it was removed by filtration and dried.

The product had a melting point of 80° to 86° C. and a yield of total tolyltriazole of 124.2 grams (93.4%).

EXAMPLE 2

Preparation of Triazoles

To a 1-liter, four-necked round bottom flask equipped with a thermometer, stirrer, a gas inlet tube and a condenser, was added 100.0 g o-phenylenediamine and 200 g 2-ethylhexanol while introducing a stream of $N_2$ through the gas inlet tube. The flask was wrapped with aluminum foil, heated to 95° C., and then was added, while stirring, 172.8 g 2-ethylhexylnitrite (92%) over a period of 35 minutes. The temperature of the reaction mixture rose to 120° C., and after initial exotherm, a reaction temperature of from 90°–95° C. was maintained for about one hour. Thereafter a mixture of 190 ml NaOH(6N) and 210 ml water was introduced. The total contents of the flask were transferred to a separatory funnel containing 400 ml water. The water layer was removed, the alcohol layer washed with 200 ml water and the combined water used was heated in the presence of about 10 g charcoal (Norite $A_{TM}$), filtered, cooled and then treated with HCl(6N) to a pH of 8.2. After the product, benzotriazole, had crystallized it was removed by filtration. 87 g of product were thus isolated. An additional 25.8 g of product were recovered from the water layer by extraction with toluene. Benzotriazole total: 113.3 g (95.2% yield).

EXAMPLES 3–14

Preparation of Triazoles

Following essentially the procedure of Example 1, additional experiments were carried out. The process condition and results are summarized in Table I.

TABLE I

| Example No. | Moles of OTDA | Solvent | Solvent q. | Nitrite (NT) | Nitrite Moles |
|---|---|---|---|---|---|
| 3 | 1.0 | NHXL | 244 | HXNT | 1.0 |
| 4 | 1.0 | ETHX | 244 | EHNT | 1.0 |
| 5 | 1.0 | ETHX | 1,000 | EHNT | 1.0 |
| 6 | 1.0 | NHXL | 1,000 | HXNT | 1.0 |
| 7 | 1.0 | ETHX | 1,000 | EHNT | 1.0 |
| 8 | 1.0 | ETHX | 800 | EHNT | 1.0 |
| 9 | 1.0 | ETHX | 700 | EHNT | 1.0 |
| 10 | 1.0 | ETHX | 500 | EHNT | 1.0 |
| 11 | 1.0 | ETHX | 500 | EHNT | 1.0 |
| 12 | 1.0 | ETHX | 500 | EHNT | 1.0 |
| 13 | 1.0 | ETHX | 500 | EHNT | 1.0 |
| 14 | 1.0 | ETHX | 250 | EHNT | 1.0 |

| Example No. | Nitrite Addition Time, Hours | Stirring Time, Hours | Total Time Hours | Reaction Temp., °C. | Yield % |
|---|---|---|---|---|---|
| 3 | 1 | 2 | 3 | 15–35 | 84 |
| 4 | 1 | 1 | 2 | 15–30 | 83 |
| 5 | 1½ | 1 | 2½ | 30–35 | 83 |
| 6 | 1 | 1 | 2 | 28–40 | 73 |
| 7 | 2 | 1 | 3 | 20–24 | 98 |
| 8 | 2½ | 2½ | 5 | 25–9 | 97 |
| 9 | 3 | 20 | 23 | 25–9 | 95 |
| 10 | 1 | 1 | 2 | 50–55 | 94 |
| 11 | ½ | ½ | 1 | 65–94 | 91 |
| 12 | ⅓ | ½ | 5/6 | 69–106 | 88 |
| 13 | ½ | 1 | 1½ | 88–105 | 95 |
| 14 | ½ | 1 | 1½ | 90–115 | 87 |

Remarks:
NHXL: n-hexanol
HXNT: n-hexyl nitrite
ETHX: 2-ethylhexanol
EHNT: 2-ethylhexyl nitrite
OTDA: o-toluenediamine

We claim:

1. A process for preparing and purifying aromatic triazoles comprising reacting a compound having the structural formula

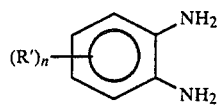

(I)

with a compound having the formula R—O—NO (II) in a reaction medium consisting essentially of a $C_6$–$C_{10}$ alkanol wherein n is zero, 1, or 2; R is $C_6$–$C_{10}$ alkyl and R' is hydrogen or $C_1$–$C_{10}$ alkyl at a temperature of 90°–120° C., said process being conducted essentially in the absence of an acid catalyst, to form the product which is then extracted into aqueous caustic, optionally treated with decolorizing charcoal, then precipitated by neutralizing the caustic layer and separating the product.

2. The process of claim 1 wherein (II) is hexyl-nitrite or 2-ethylhexyl nitrite, the solvent is n-hexanol, or 2-ethylhexanol, and (I) is 1,2-phenylenediamine or o-toluenediamine.

3. The process of claim 2 wherein the triazole is benzotriazole or tolyltriazole.

* * * * *